United States Patent [19]

Keith

[11] 4,428,925

[45] Jan. 31, 1984

[54] SUSTAINED RELEASE GLYCEROL TRINITRATE

[75] Inventor: Alec D. Keith, Miami, Fla.

[73] Assignee: Key Pharmaceuticals, Inc., Miami, Fla.

[21] Appl. No.: 425,282

[22] Filed: Sep. 28, 1982

Related U.S. Application Data

[63] Continuation of Ser. No. 332,127, Dec. 18, 1981, abandoned.

[51] Int. Cl.³ .......................... A61K 9/22; A61K 9/24; A61K 9/32
[52] U.S. Cl. ...................................... 424/19
[58] Field of Search ..................... 424/19–22, 424/32, 33

[56] References Cited

U.S. PATENT DOCUMENTS

| | | | |
|---|---|---|---|
| 2,693,438 | 11/1954 | Ward | 424/33 |
| 3,096,248 | 7/1963 | Rudzki | 424/32 |
| 3,832,470 | 8/1974 | Russek | 424/330 |
| 3,935,326 | 1/1976 | Groppenbacher et al. | 424/33 |
| 3,951,821 | 4/1976 | Davidson | 424/15 |
| 4,060,598 | 11/1977 | Groppenbacher et al. | 424/33 |
| 4,235,870 | 11/1980 | Leslie | 424/35 |
| 4,248,856 | 2/1981 | Guley et al. | 424/33 |
| 4,248,857 | 2/1981 | DeNeale et al. | 424/33 |
| 4,248,858 | 2/1981 | Guley et al. | 424/33 |
| 4,249,531 | 2/1981 | Heller et al. | 424/33 |
| 4,330,338 | 5/1982 | Banker | 424/33 |

FOREIGN PATENT DOCUMENTS

| | | | |
|---|---|---|---|
| 2363853 | 7/1975 | Fed. Rep. of Germany | 424/33 |
| 45-1274 | 1/1970 | Japan | 424/32 |
| 54-28812 | 3/1979 | Japan | 424/32 |
| 55-49312 | 4/1980 | Japan | 424/32 |
| 56-110612 | 9/1981 | Japan | 424/33 |
| 1213348 | 11/1970 | United Kingdom | 424/32 |

*Primary Examiner*—Shep K. Rose
*Attorney, Agent, or Firm*—Wegner & Bretschneider

[57] ABSTRACT

Glycerol trinitrate is delivered orally in a sustained release dosage form. The dosage form is for oral administration and comprises a core containing the drug and a coating of an expandable lattice, said expandable lattice permitting the passage of water therethrough but which under conditions of high pressure is expanded to a state whereby molecules of the drug are permitted to pass therethrough, said expandable lattice retaining its structural integrity, said dosage form when contacted with the aqueous medium of the gastro-intestinal tract taking up water in said core through passage of water through said expandable lattice, whereby an osmotic pressure is built up causing said expandable lattice to expand responsive to said osmotic pressure, the drug being permitted to escape through the resultant expanded lattice structure of said expandable lattice.

5 Claims, No Drawings

SUSTAINED RELEASE GLYCEROL TRINITRATE

This application is a continuation of U.S. application Ser. No. 332,127, filed Dec. 18, 1981, abandoned.

SUMMARY OF THE INVENTION

Glycerol trinitrate is a well known dosage form for the treatments of angina pectoris and sometimes for other cardiac related conditions. Medication forms range from ointments supplied directly to the skin to sublingual tablets designed to disintegrate under the tongue, conventional oral tablets, and long lasting oral tablets. In recent times it has been generally thought that the long lasting oral dosage forms are inferior to sublingual or topically applied forms for the simple reason that the liver is a major metabolic destructive site for nitroglycerin. By using a sublingual or topically applied dosage form the liver is largely bypassed in getting to the target site for activity of this drug. Oral dosage forms work in such a way that the nitroglycerin is absorbed from the intestinal tract into the intestinal circulation and there passes through the portal circulation and liver before traversing to the target site for activity.

One approach to overcoming drug destruction effect in liver is to supply larger doses to patients than would ordinarily be supplied by calculations derived from sublingual or topical dosage forms so as to overwhelm liver metabolism. Tablet forms of medication have been shown in the historical development of pharmacology and therapeutics in general to be a highly desirable form of medication. Patients are well trained in the act of taking tablets. Tablets present a convenient form of medication for patients to carry during travels or through their normal daily activities. One approach to overcome or partially overcome the effect of the liver is for the patient to take a compensating higher dose than would ordinarily be taken to overwhelm the liver metabolism and therefore allow a significant or therapeutic concentration of nitroglycerin to filter through the liver.

A dosage form is provided for oral administration of glycerol trinitrate to a patient which comprises a core containing the drug and a coating of an expandable lattice, said expandable lattice permitting the passage of water therethrough resulting in dissolution of the drug and which under conditions of osmotic pressure is expanded to a state whereby molecules of the drug are permitted to pass therethrough, said expandable lattice retaining its structural integrity, said dosage form when contacted with the aqueous medium of the gastro-intestinal tract taking up water in said core through passage of water through said expandable lattice, whereby an osmotic pressure is built up causing said expandable lattice to expand responsive to said osmotic pressure, said drug being permitted to escape through the resultant expanded lattice structure of said expandable lattice.

In a preferred embodiment, the expandable lattice contains polyvinyl alcohol, preferably having a molecular weight of at least 75,000. In a particularly preferred embodiment, the expandable lattice contains polyvinyl alcohol having a molecular weight of from about 75,000 to about 150,000. In a further embodiment, the expandable lattic also contains polyethyleneglycol having a molecular weight of from about 400 to about 4000.

DETAILED DESCRIPTION OF THE INVENTION

In accordance with the present invention, tablets covered with an expandable lattice are provided that take advantage of the osmotic pressure phenomenon, the expandable lattice providing for the passage of water therethrough, but not for exit of the glycerol trinitrate inside the tablet when the tablet has not been subjected to an osmotic pressure. Unlike tablets with a laser-drilled hole or burstable tablets of the prior art, the expandable lattice of the present invention does not rupture or crack. Instead, the expandable lattice is of a homogeneous polymeric material which when subjected to osmotic pressure expands its lattice structure to permit the expulsion of solubilized drug. Confirmation of this mechanism had been experimentally observed through the use of large and small dye molecules, each of a distinctive color. The larger dye molecule was polymerically bonded to be of a very large size. When tablets were formulated with an expandable lattice in accordance with the present invention through an air suspension coating procedure on a Glatt column, having inside the two dye molecules of different colors, it was observed after putting such tablets in water that only the color of the smaller dye molecule diffused out through the "skin" of the tablet into the aqueous environment, i.e., only the color of the smaller dye was observed. The absence of the color of the larger polymerized dye molecule confirmed that the expandable lattice had not ruptured.

In a preferred embodiment, there is provided as the expandable lattice a polymer based upon polyvinyl alcohol and polyethyleneglycol (PEG). The polyvinyl alcohol has a molecular weight generally in excess of about 75,000 and still more preferably in excess of 90,000, and a maximum which is dictated only by the ease of preparation of the polymer, generally about 150,000 being a maximum for practical purposes. In a preferred embodiment, polyvinyl alcohol having a molecular weight of 115,000 is used. The degree of hydrolysis should be relatively high. In a preferred embodiment the degree of hydrolysis should generally be above about 90%, and still more preferably at least 95%. In experiments a degree of hydrolysis of about 98% was found particularly suitable. The polyethyleneglycol generally has a molecular weight of from about 400 to about 4000, and still more preferably about 800 to about 1500. In experiments that have been conducted a molecular weight of 1000 has been used.

The relative amounts of the polyvinyl alcohol and the polyethyleneglycol may vary greatly, depending upon the properties that are desired of the expanded lattice. In one embodiment, where it is desired to have a polymer coating that will not lose its structural integrity during the extreme osmotic pressure to which it is to be subjected, the polyvinyl alcohol is present generally in a larger amount than the polyethyleneglycol, and preferably in a weight ratio of polyvinyl alcohol to polyethyleneglycol of about 9:1. In a further embodiment where an at least partial erosion of the expanding lattice is desired for faster release of the drug, a larger percentage of polyethyleneglycol is desirable. In one embodiment polyethyleneglycol is present at about 20% the weight amount of the polyvinyl alcohol.

The total percentage of polyvinyl alcohol is generally from about 5 to 20% by weight (before drying of the polymeric material), and about 15% being a preferred embodiment. (The "wet" calculation is based upon the maximum concentration in an aqueous medium which still permits full polymer extension and workability).

The total amount of the polyethyleneglycol for an embodiment where no erosion of the polymer lattice is desired will generally be about 1/10th the weight of the polyvinyl alcohol, e.g., the polyethyleneglycol will generally be present in an amount of from about 0.1 to about 5% by weight. With erosion being desired, the weight will generally be from about 1 to about 10% polyethyleneglycol. With a 15% polyvinyl alcohol content in the first embodiment of the present invention, about 1 to about 2% polyethyleneglycol is preferred, and still more preferably about 1.5% by weight polyethyleneglycol.

A lattice enhancer which promotes hydrogen bonding is suitably included in the polymer, including triethanolamine, sugars, citrate, tris-hydroxyaminomethane, phosphates, borates, and other hydrogen-bonding crosslinkers. A preferred lattice enhancer is tris-hydroxyaminomethane (TRIS). TRIS in the amount of from about 0.1 to about 1% is particularly suited.

For organic base drugs it is preferred to have a expandable lattice having a pH-adjustable character. It is therefore advantageous for such basic drugs to have as a lattice enhancer a pH-buffer compound itself, as exemplified by TRIS and triethanolamine. Such lattice enhancers of a basic nature may be used for non-basic drugs as well, and if desired the charge may be neutralized through use of a salt form. For example, to operate at a neutral pH, TRIS hydrochloride would be preferred over TRIS itself.

The amount of the drug will be dictated by a consideration of the total amount that is desired for the period of release taken together with the amount that will be released from the polymeric membrane. It is generally contemplated that the entire amount of the drug may be released in the gastro-intestinal tract.

The degree of rate of expulsion is controlled not only through the selection of the particular polymeric coating components of the expandable lattice, but also through the amount and type of solid material inside the tablet which will affect the osmotic pressure, the osmotic pressure being a driving force in the determination of the rate of release of the drug. Small molecules that are pharmaceutically inert may be advantageously included with the drug inside the variably permeable membrane. A sugar such as sucrose may be used or a less soluble sugar such as lactose may be used as examples of embodiments of the present invention, lactose tending to remain in the membrane enclosure for a longer period of time than sucrose, such osmotic pressure helping to push the drug out from the variably permeable membrane.

As an osmotic attractant may be mentioned methocel. Any relatively water insoluble but hygroscopic polymer such as cellulose and cellulose derivatives may be used to replace methocel. Other polymers containing hydration sites may be used. Sucrose is a further preferred osmotic attractrant. A variety of sugars may be used to replace sucrose. A general requirement for the sugar is that the sugar should be on the same order of size as the drug to be delivered. It is also suitable for the sugar to be larger than the drug. It is usually not suitable for the sugar to be substantially smaller than the drug to be delivered, because the mechanism of action of the expandable lattice is such that the osmotic-mediated expansion of the matrix will expand to allow the sugar to be released, but, if the drug to be delivered is substantially larger than the sugar, then the drug will be retained. Therefore, in expanding the lattice so that the sugar may be released, it is important to keep conditions such that the drug is also released. Among the necessary conditions to cause this to come about is to always insure that the sugar is on the same size or larger than the drug. Magnesium stearate may be replaced with other suitable tablet lubricants.

The following non-limiting example serve to further illustrate the invention:

EXAMPLE

An oral medical form of nitroglycerin is constructed such that the nitroglycerin is released over a 12-hour period. This medication is composed of a conventional tablet containing nitroglycerin and is film coated with a polymer coat to effect the release kinetics. The tablet contains 125 parts lactosetriturate (10% glycerol trinate), 5 parts magnesium stearate, 60 parts sucrose, and 40 parts methocel. Film coating for the glycerol trinitrate: lactose system is treated in the following way. The final mass of this tablet is 252 mg. This tablet is coated with 20 mg per tablet of the polymer coating material:

| Polyvinylalcohol | 115,000 mw | 9 parts |
|---|---|---|
| Polyethylene glycol | 1,000 mw | 1 part |

The final tablet therefore weighs 272 mg resulting in 7.4% coating material. For the tablet given above the coating material polyvinyl alcohol and polyethyleneglycol at a ratio of 9:1 was made up of a 5% concentration in methanol water. A tablet coated in this manner gives the release kinetics shown in FIG. 3. This has been carried out in two separate batches as is illustrated by two separate lines. A similar batch was made up using tablets of the same size only in this case using 8% tablet coating to result in the release kinetics shown in FIG. 4.

Glycerol trinitrate:polyvinyl alcohol triturate may also be used in the formulations given above by simply substituting the glycerol trinitrate:polyvinyl alcohol triturate for the glycerol trinitrate:lactose triturate. The glycerol trinitrate:polyvinyl alcohol triturate is composed of 10% nitroglycerin 90% polymer. The polyvinyl alcohol polymer is generally 10,000 mw 88% hydrolyzed polyvinylalcohol. Preparation of this triturate is disclosed in my earlier filed U.S. application Ser. No. 281,389, filed July 8, 1981.

In order to facilitate the time release of glycerol trinitrate it may be desired to modify pH constraints within the membrane (polymer film) structure. TRIS (tris-hydroxy-amnomethane) may be used in small quantities (0.1 to 3% of the polymer content) in order to facilitate strength and a desired pH environment. TRIS acts both as a pH buffer and as a hydrogen-bonding catalyst. Since TRIS has three hydroxyls and one amine group, it is a suitable molecule for the bridging of hydrogen donors or hydrogen acceptor sites. The same coating system may be used for a variety of medication-containing tablets.

What is claimed is:

1. A dosage form for oral administration of glycerol trinitrate to a patient which comprises a core containing glycerol trinitrate and a coating of about 5–10% by weight of an expandable, above about 90% hydrolyzed polyvinyl alcohol molecular weight of about 75,000 to about 150,000, lattice containing from about 1% up to 10% of polyethylene glycol having a molecular weight of about 400 to about 4000, said coating permeable to water but not glycerol trinitrate, said dosage form when contacted with the aqueous medium of the patient's gastro-intestinal tract taking up water in said core by passage of water through said lattice and the resultant increase in osmotic pressure in the core expanding the lattice and making it permeable to glycerol trinitrate, said lattice retaining its structural integrity.

2. A dosage form according to claim 1 wherein the polyvinyl alcohol has a molecular weight between about 90,000 to 115,000.

3. A dosage form according to claim 2 containing a hygroscopic osmotic attractant polymer or sugar incorporated in its core.

4. A dosage form according to claim 1 containing a lattice enhancing buffering agent incorporated in its lattice.

5. A method of providing a patient with sustained release of glycerol trinitrate over a long period of time which comprises orally administrating to said patient a dosage form of claim 1.

* * * * *